United States Patent
Gurjar et al.

(10) Patent No.: US 10,759,738 B2
(45) Date of Patent: Sep. 1, 2020

(54) PROCESS FOR PREPARATION OF ISOPROTERENOL HYDROCHLORIDE

(71) Applicant: EMCURE PHARMACEUTICALS LIMITED, Bhosari, Pune (IN)

(72) Inventors: Mukund Keshav Gurjar, Pune (IN); Shashikant Gangaram Joshi, Pune (IN); Jagannath Tulsiram Jagtap, Pune (IN); Sachin Arvind Badhe, Pune (IN)

(73) Assignee: EMCURE PHARMACEUTICALS LIMITED, Bhosari, Pune (IN)

( * ) Notice: Subject to any disclaimer, the term of this patent is extended or adjusted under 35 U.S.C. 154(b) by 0 days.

(21) Appl. No.: 16/473,546

(22) PCT Filed: Jan. 3, 2018

(86) PCT No.: PCT/IB2018/050031
§ 371 (c)(1),
(2) Date: Jun. 25, 2019

(87) PCT Pub. No.: WO2018/127806
PCT Pub. Date: Jul. 12, 2018

(65) Prior Publication Data
US 2019/0367443 A1    Dec. 5, 2019

(30) Foreign Application Priority Data

Jan. 7, 2017 (IN) .............................. 201721000708

(51) Int. Cl.
| | |
|---|---|
| *C07C 213/04* | (2006.01) |
| *C07C 213/08* | (2006.01) |
| *C07C 215/60* | (2006.01) |
| *C07C 215/66* | (2006.01) |

(52) U.S. Cl.
CPC .......... *C07C 213/04* (2013.01); *C07C 213/08* (2013.01); *C07C 215/60* (2013.01); *C07C 215/66* (2013.01)

(58) Field of Classification Search
CPC ... C07C 213/04; C07C 213/08; C07C 215/60; C07C 215/66
See application file for complete search history.

(56) References Cited

U.S. PATENT DOCUMENTS

| | | |
|---|---|---|
| 2,308,232 A | 1/1943 | Scheuing et al. |
| 2,715,141 A | 8/1955 | Delmar et al. |
| 5,442,118 A | 8/1995 | Gao et al. |

FOREIGN PATENT DOCUMENTS

| | | |
|---|---|---|
| AT | 178353 | 5/1954 |
| CN | 107011188 | 8/2017 |

OTHER PUBLICATIONS

Corrigan et al., "Preparation of N-Substituted 1-(3',4'-Dihydroxyphenyl)-2-Aminoethanols" Journal of the American Chemical Society, Feb. 1949 pp. 530-531.
PCT International Search Report for PCT/IB2018/050031, dated Apr. 11, 2018.
PCT Search Strategy Document for PCT/IB2018/050031, Jul. 2018.
PCT Written Opinion for PCT/IB2018/050031, dated Jul. 2018.

*Primary Examiner* — Jafar F Parsa
(74) *Attorney, Agent, or Firm* — Florek & Endres PLLC

(57) ABSTRACT

The present invention provides a process for preparation of isoproterenol hydrochloride (1a) comprising catalytic hydrogenation of 3',4'-dihydroxy-2-(isopropylamino)-acetophenone hydrochloride (5a) in presence of an ion exchange resin, to provide isoproterenol hydrochloride (1a).

10 Claims, No Drawings

PROCESS FOR PREPARATION OF ISOPROTERENOL HYDROCHLORIDE

This application is the U.S. National Stage filing of International Patent Application Number PCT/IB2018/050031, filed on Jan. 3, 2018, which claims the benefit of Indian Provisional Applications No. 201721000708 filed on 7 Jan. 2017, which is hereby incorporated by reference in its entirety.

FIELD OF THE INVENTION

The present invention relates to an industrially applicable process for preparation of isoproterenol hydrochloride (1a). The invention specifically relates to the use of an ion exchange resin during hydrogenation of the intermediate 3',4'-dihydroxy-2-(isopropylamino)acetophenone which exerts significant control on impurities and provides isoproterenol hydrochloride in good yield with desired purity.

BACKGROUND OF THE INVENTION

Isoproterenol hydrochloride (1a), chemically identified as hydrochloride salt of 3,4-dihydroxy-α-[(isopropylamino) methyl]benzyl alcohol or 1-(3,4-dihydroxyphenyl)-2-isopropylaminoethanol is represented as given below.

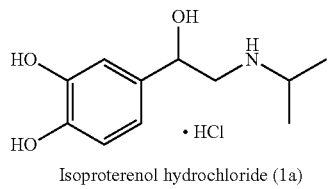

Isoproterenol hydrochloride (1a)

Isoproterenol, an isopropyl analog of epinephrine is a non-selective β-adrenoreceptor agonist and TAAR1 agonist which exhibits f-sympathomimetic action on the beta receptors of heart, bronchi, skeletal muscle, alimentary tract etc. It is employed for the treatment of bradycardia (slow heart rate), heart block, and rarely for asthma. Isoproterenol is a potent nonselective beta-adrenergic agonist with very low affinity for alpha-adrenergic receptors.

Isoproterenol hydrochloride injection is indicated in the following conditions.

a) Mild or transient episodes of heart block that do not require electric shock or pacemaker therapy, b) Serious episodes of heart block and Adams-Stokes attacks c) In cardiac arrest until electric shock or pacemaker therapy is available.

d) Bronchospasm occurring during anesthesia and e) As an adjunct to fluid and electrolyte replacement therapy Generic version of isoproterenol hydrochloride is marketed by Nexus Pharmaceuticals Inc., while Hospira Inc. markets it under the trade name Isuprel; both of which are injectables with the strength of 0.2 mg/ml.

U.S. Pat. No. 2,308,232 discloses a process for the preparation of isoproterenol comprising reaction of 3,5-dihydroxyphenyl-ω-chloroacetophenone with excess of isopropylamine, using ethanol as solvent, followed by palladium, platinum or nickel catalyzed hydrogenation of the resulting isopropylamino acetophenone derivative to yield the desired product. The disclosed process reveals that in order to achieve the desired purity, both the ketone intermediate and final compound need to be purified through their respective salt formation followed by crystallization. This clearly indicates formation of impurities in significant proportions, thereby adversely affecting the yield and making the process industrially unviable.

AT 178353 and U.S. Pat. No. 2,715,141 disclose processes for separation of the desired enantiomer of isoproterenol comprising treatment of the racemic mixture with d-tartaric acid. The method comprises dissolving a mixture of isoproterenol sulfate and D-tartaric acid in water and treating with barium hydroxide. Filtration of barium sulfate precipitate, concentration of the filtrate, and further resolution of the concentrate by fractional crystallization using methanol and acetone provides optically active isoproterenol.

U.S. Pat. No. 5,442,118 discloses a method for preparation of enantiopure isoproterenol comprising use of a borane reducing agent, and a chiral 1, 3, 2-oxazaborole derivative catalyst. In this method, treatment of corresponding acetophenone with HBr in DMSO, followed by reaction with water provides the arylglyoxal derivative, which, after reaction with the appropriate amine gives ketoimine derivative. Reduction of the ketoimine using the organoboranes like $Me_2S$—$BH_3$ in presence of said oxazaborole catalysts provides isoproterenol.

CN 107011188 discloses Friedel-Crafts reaction of catechol and glycine in the presence of zinc chloride to give 2-amino-1-(3,4-dihydroxy phenyl)ethanone, which after reaction with isopropyl chloride and catalytic hydrogenation provides isoproterenol.

It is evident from the study of prior art that conventional synthetic methods reported for isoproterenol suffer from formation of impurities in significant proportions. In these methods, undesired impurities such as impurity-A are generated during the final stage of ketone-reduction. These impurities, being structurally similar to isoproterenol, are difficult to remove during work up procedures and thus necessitate steps like chromatographic purifications or repeated crystallization procedures. This causes increase in number of procedural steps; resulting in significant yield loss and ultimately, substantially increased project cost.

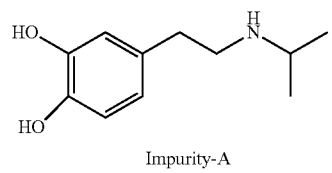

Impurity-A

To circumvent the challenge of associated impurities generated during the aforementioned reactions, some synthetic methods reported in prior art have resorted to use of highly specific intermediates like keto-imines. However, this requires use of specific reagents, adds to the number of synthetic steps and increases the project cost.

Hence, there is a need to have a cost effective, industrially applicable process which avoids use of expensive catalysts, significantly controls the formation of impurities such as impurity-A and provides isoproterenol having desired purity.

The present inventors have developed a robust and commercially viable synthetic method which avoids the shortcomings in the prior art and provides isoproterenol hydrochloride (1a) conforming to regulatory specifications.

OBJECT OF THE INVENTION

An objective of the present invention is to provide a cost-effective and convenient process for the synthesis of isoproterenol hydrochloride (1a) which does not involve expensive reagents, or unstable, labile intermediates and which can easily be scaled up to a commercially viable process.

Another object of the invention is to provide isoproterenol hydrochloride (1a) with good yield and purity wherein the impurity levels conform to the regulatory norms.

SUMMARY OF THE INVENTION

The present invention relates to an improved process for the preparation of isoproterenol hydrochloride (1a) which overcomes limitations in the prior art methods.

An aspect of the present invention relates to an improved and cost-effective process for the preparation of isoproterenol hydrochloride (1a), comprising treatment of 2-chloro-3',4'-dihydroxy acetophenone (4) with isopropyl amine and hydrochloric acid to provide 3',4'-dihydroxy-2-(isopropylamino)-acetophenone hydrochloride (5a), followed by hydrogenation in presence of an ion exchange resin to provide isoproterenol hydrochloride (1a) having desired purity.

Another aspect of the present invention relates to an improved and cost-effective process for the preparation of isoproterenol hydrochloride (1a), comprising treatment of 2-chloro-3',4'-dihydroxy acetophenone (4) with isopropyl amine and hydrochloric acid to provide 3',4'-dihydroxy-2-(isopropylamino)-acetophenone hydrochloride (5a), followed by hydrogenation in presence of palladium catalyst and a weakly basic resin provides isoproterenol hydrochloride (1a) having desired purity.

The following detailed description will make the objectives of the present invention fully apparent.

DETAILED DESCRIPTION OF THE INVENTION

The present inventors, while working on development of a convenient, cost effective, industrially applicable process for synthesis of isoproterenol, carried out extensive experimentation which primarily focused on controlling the formation of impurities.

Accordingly, various synthetic routes, with different hydroxyl protecting groups as well as varied reaction parameters were studied for synthesis of isoproterenol. It was observed that undesired side products, associated impurities were inevitably formed during the final step of reduction of ketone intermediate. Impurity-A, amongst others, was formed to the extent of 1-2% during the course of reaction. The inventors also observed that removal of impurity-A, which was formed at the final stage was particularly difficult due to its structural similarity with isoproterenol. The purification technique required was column chromatographic purification followed by repeated crystallizations which then provided isoproterenol with impurity-A barely at the threshold limit of 0.1%. However, they were time-consuming and required large amounts of solvents, or solvent mixtures and hence proved to be uneconomical and thus not suitable for industrial use.

It was surprisingly found by the inventors that during the hydrogenation reaction of the intermediate 3',4'-dihydroxy-2-(isopropylamino)-acetophenone use of ion exchange resins significantly restricted the formation of impurity-A. This unexpected observation proved to be advantageous in a number of ways as given below.

1. The resins were commercially available, and hence could be procured easily for industrial scale application.
2. The resins were required in small quantity and could be recycled after solvent washing and activation, making them highly cost-effective additives for each batch run.
3. When the impurity formation itself was controlled, other steps such as chromatographic purification or crystallization were not required.
4. With the use of the said resins, which are preferably weakly basic in nature, impurity-A was brought down well below 0.1%, without any chromatographic purification and which resulted in a clean, robust and economical process for synthesis of isoproterenol hydrochloride.
5. Due to ready availability of the resins and elimination of time-consuming recrystallization steps, the process was easily scaled up for industrial application.

Scheme 1: Method embodied in the present invention for preparation of isoproterenol hydrochloride (1a)

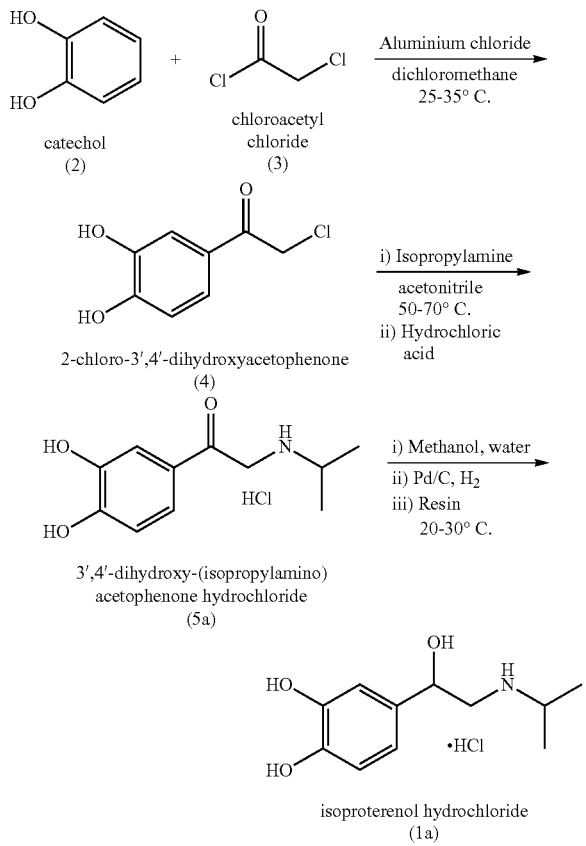

In an embodiment, catechol of formula (2) was treated with chloroacetyl chloride (3) in presence of aluminium chloride and solvent dichloromethane in the temperature range of 0-45° C. After completion of the reaction, as monitored by HPLC, the resultant reaction mixture was treated with acid and filtered to give 2-chloro-3',4'-dihydroxy acetophenone (4).

Further reaction of compound (4) with isopropyl amine to give 3',4'-dihydroxy-2-(isopropylamino)-acetophenone (5)

was carried out in presence of an organic solvent in the temperature range of 50-70° C. The organic solvent was selected from aprotic solvents such as acetonitrile, tetrahydrofuran, dimethyl sulfoxide, dimethyl formamide, dimethyl acetamide and mixtures thereof.

After completion of the reaction, as monitored by HPLC, the reaction mixture was treated with hydrochloric acid and filtered to provide 3',4'-dihydroxy-2-(isopropylamino)acetophenone hydrochloride (5a).

Compound (5a) was subjected to hydrogenation in presence of a palladium catalyst, and a resin in the temperature range of 20-30° C. The reaction was carried out using alcoholic solvent such as methanol, ethanol, isopropanol, optionally mixed with water, under the hydrogen pressure in the range of 2 to 8 Kg/cm$^2$.

The resin was selected from a group of ion-exchange resins such as Amberlite IRA-900 CI, Amberlite IRA-904, Amberlyst A-21. Amberlyst A-26 OH, Amberlyst A-27, Indion 850 etc. Anion exchange resin such as Amberlyst A-21 having weakly basic properties was preferably used. The amount of resin used during the hydrogenation was in catalytic amounts, ranging from 1-10%, hence, possibility of any side reaction due to the presence of resins was eliminated.

After completion of the reaction, as monitored by HPLC, the reaction mixture was filtered and the filtrate was concentrated after optional treatment with activated carbon to yield a residue, which was treated with alcohol and water to afford isoproterenol hydrochloride (1a).

The following examples are meant to be illustrative of the present invention. These examples exemplify the invention and are not to be construed as limiting the scope of the invention.

EXAMPLES

Example 1: Preparation of 2-chloro-3',4'-dihydroxy acetophenone (4)

Catechol (2, 200 g) was added lot-wise to the mixture of aluminium chloride (606 g) and dichloromethane (1800 ml) at 0-10° C. followed by gradual addition of chloroacetyl chloride (3, 217.3 g) in 2(10 ml dichloromethane at 0-10° C. The reaction mixture was stirred at 25-35° C. till completion of the reaction as monitored by HPLC. The reaction mass was quenched with aqueous hydrochloric acid followed by filtration to isolate the crude product. Isolation from aqueous acetic acid gave the desired compound, 2-chloro-3',4'-dihydroxy acetophenone (4).

Yield: 210 g; (62%).

Example 2: Preparation of 3',4'-dihydroxy-2-(isopropylamino)-acetophenone Hydrochloride (5a)

2-chloro-3',4'-dihydroxy acetophenone (4, 200 g) was added to acetonitrile (1400 ml) placed in a round bottom flask. Isopropyl amine solution (221.7 g) was gradually added to the mixture at 20-30° C. The reaction temperature was raised to 55-65° C. and continued till completion of the reaction, as monitored by HPLC.

The reaction mixture was cooled to 20-30° C. and concentrated hydrochloric acid (383 ml) was gradually added to it, till the pH was around 2.0. The reaction mixture was heated to 50-65° C., with stirring, cooled and filtered to give crude 3',4'-dihydroxy-2-(isopropylamino)-acetophenone hydrochloride (50).

Yield: 120 g; (45%).

Example 3: Preparation of Isoproterenol Hydrochloride (1a)

Methanol (800 ml) was placed in an autoclave and 3',4'-dihydroxy-2-(isopropylamino)-acetophenone hydrochloride (5a, 100 g), Pd/C (10%, moisture 50%, 10 g.), were added to it as a slurry in methanol, along with water (60 ml) and Amberlyst A-21 resin (1 g). The reaction was carried out at 20-30° C. in presence of hydrogen gas (3 to 5 Kg/cm$^2$) which was maintained till completion of the reaction. After reaction completion, as monitored by HPLC, the reaction mixture was filtered and the filtrate was concentrated after optional treatment with activated carbon. The solid thus obtained was treated with ethanol and water followed by filtration to give isoproterenol hydrochloride (1a).

Yield: 66.4 g (65.5%)

Purity: 99.93% (HPLC).

We claim:

1. A process for the preparation of isoproterenol hydrochloride of formula (1a) comprising reacting catechol (2) with chloroacetyl chloride (3) in presence of aluminium chloride to give 2-chloro-3',4'-dihydroxy acetophenone (4), reacting 2-chloro-3',4'-dihydroxy acetophenone (4) with isopropyl amine in an organic solvent, treating the reaction product with hydrochloric acid to give 3',4'-dihydroxy-2-(isopropylamino)-acetophenone hydrochloride (5a), and hydrogenating 3',4'-dihydroxy-2-(isopropylamino)-acetophenone hydrochloride (5a) in the presence of a resin to provide isoproterenol hydrochloride of formula (1a).

2. A process for the preparation of isoproterenol hydrochloride of formula (1a) comprising hydrogenating of 3',4'-dihydroxy-2-(isopropylamino)acetophenone hydrochloride (5a) in presence of a resin to provide isoproterenol hydrochloride of formula (1a).

3. The process as claimed in claim 2 wherein the hydrogenation is carried out using 3',4'-dihydroxy-2-(isopropylamino)acetophenone (5) to provide isoproterenol (1).

4. The process as claimed in claim 1, wherein the resin is an ion exchange resin.

5. The process as claimed in claim 4, wherein the ion exchange resin is selected from Amberlite IRA-900 CI, Amberlite IRA-904, Amberlyst A-21, Amberlyst A-26 OH, Amberlyst A-27, and Indion 850.

6. The process as claimed in claim 4, wherein the ion exchange resin is a weakly basic resin.

7. The process as claimed in claim 1, wherein the organic solvent is selected from dimethyl formamide, tetrahydrofuran, acetonitrile, dimethyl sulfoxide, dimethyl acetamide and combinations thereof.

8. The process as claimed in claim 2, wherein the resin is an ion exchange resin.

9. The process as claimed in claim 8, wherein the ion exchange resin is selected from Amberlite IRA-900 CI, Amberlite IRA-904, Amberlyst A-21, Amberlyst A-26 OH, Amberlyst A-27, and Indion 850.

10. The process as claimed in claim 8, wherein the ion exchange resin is a weakly basic resin.

* * * * *